(12) United States Patent
Jeong et al.

(10) Patent No.: US 8,363,921 B2
(45) Date of Patent: Jan. 29, 2013

(54) STEEL BRIDGE COATING INSPECTION SYSTEM USING IMAGE PROCESSING AND THE PROCESSING METHOD FOR THE SAME

(75) Inventors: Haimoon Jeong, Yongin-si (KR); Chan-Young Lee, Hwaseong-si (KR); Whoi-Yul Kim, Seoul (KR); Jong-Min Lee, Hanam-si (KR); Ki-Hong Park, Seoul (KR)

(73) Assignee: Korea Expressway Corporation, Seongnam-Si, Gyonggi-Do (KR)

( * ) Notice: Subject to any disclaimer, the term of this patent is extended or adjusted under 35 U.S.C. 154(b) by 326 days.

(21) Appl. No.: 12/675,546

(22) PCT Filed: Apr. 18, 2008

(86) PCT No.: PCT/KR2008/002190
§ 371 (c)(1),
(2), (4) Date: Feb. 26, 2010

(87) PCT Pub. No.: WO2009/031743
PCT Pub. Date: Mar. 12, 2009

(65) Prior Publication Data
US 2011/0150326 A1 Jun. 23, 2011

(30) Foreign Application Priority Data
Sep. 3, 2007 (KR) .................. 10-2007-0088807

(51) Int. Cl.
G06K 9/00 (2006.01)
(52) U.S. Cl. .................. 382/141; 356/237.1; 356/237.6
(58) Field of Classification Search .... 356/237.1–237.6; 382/141
See application file for complete search history.

(56) References Cited

U.S. PATENT DOCUMENTS

| | | | |
|---|---|---|---|
| 5,991,018 A | 11/1999 | Imaizumi et al. | |
| 6,532,066 B1 * | 3/2003 | Filev et al. | 356/237.2 |
| 6,714,831 B2 * | 3/2004 | Matthews et al. | 700/110 |
| 6,947,797 B2 * | 9/2005 | Dean et al. | 700/79 |
| 2003/0139836 A1 * | 7/2003 | Matthews et al. | 700/110 |
| 2007/0031026 A1 * | 2/2007 | Kurihara et al. | 382/149 |
| 2007/0286478 A1 * | 12/2007 | Kishi | 382/162 |

* cited by examiner

FOREIGN PATENT DOCUMENTS

| | | | |
|---|---|---|---|
| JP | 2004-020498 A | | 1/2004 |
| KR | 10-2004-0041243 A | | 5/2004 |

OTHER PUBLICATIONS

International Search Report of International Application No. PCT/KR2008/002190.

*Primary Examiner* — Tarifur Chowdhury
*Assistant Examiner* — Isiaka Akanbi
(74) *Attorney, Agent, or Firm* — Kile Park Goekjian Reed & McManus PLLC

(57) ABSTRACT

An inspection system and method for paint coated film of steel bridge using image processing technique including a paint coated film image storing process that stores in a data base (DB) unit a paint coated film image information of a steel bridge photographed by the inspection system; a paint coated film information loading process that loads information stored in the DB unit through calling a file containing the paint coated film image information to be inspected; a scale and rust extracting process that displays a scale part and a rust part on an output unit after detecting the rust part and the scale part by use of the inspection system and storing a calculated percentage of deteriorated are in the DB unit; and a repainting information calculating process that calculates a time for repainting and provide an optimum method for paint coating by deteriorated image information of paint coated film.

8 Claims, 12 Drawing Sheets

FIG. 7

<DETAILED COATED FILM DIAGNOSIS EFFECT>

① JINWICHEON BRIDGE COATING CHECK TABLE

| BRIDGE NAME | JINWICHEON | ROUTE | Seoul & Busan line | DISTANCE | 16km |
|---|---|---|---|---|---|
| BRANCH | Daegu branch | ADDRESS | 11 | BRIDGE TYPE | 11 |
| INSTALLATION ENVIRONMENT | seashore | INSTALLATION YEAR | 1231 | REPAIR PAINT COATED FILM | good |

② PAINT COATING RECORD

| THE NUMBER OF PAINT COATING | PAINT COATING YEAR | PAINT COATING TYPE | ROAD MAKER | PAINT COATING COMPANY |
|---|---|---|---|---|
| The beginning paint coating | 1998 | | | |
| The first repair paint coating | 1999 | | | |
| The second repair paint coating | 2000 | | | |
| The third repair paint coating | 2001 | | | |
| The fourth repair paint coating | 2002 | | | |
| The fifth repair paint coating | 2003 | | | |
| The sixth repair paint coating | 2004 | | | |
| The seventh repair paint coating | 2005 | | | |

③ COATED FILM DIAGNOSIS EFFECT

| DIAGNOSIS DATE | RUST | PEELING OFF | EXCEPT | SYNTHETIC JUDGEMENT |
|---|---|---|---|---|
| 2005. 11. 07 | 0 point(0%) | 0 point(0%) | 0 point | IV |
| 2005. 07. 05 | 40 points(11.1%) | 12 points(6.76%) | 3 points | II |
| 2005. 01. 24 | 0 point(0%) | 18 points(11%) | 0 point | IV |

④ DETAILED COATED FILM EVALUATION OF JINWICHEON BRIDGE

| CHECK DATE | RUST | PEELING OFF | EXCEPT | SYNTHETIC JUDGEMENT |
|---|---|---|---|---|
| 2005. 11. 07 | 0 point(0%) | 0 point(0%) | 0 point | IV |
| FOLLOW-UP MEASURES | repair paint coating not required | | | |

| BRIDGE BETWEEN | PART | PICTURE | PAINT COATED FILM DETERIORATION EVALUATION | | |
|---|---|---|---|---|---|
| The first bridge between | middle board | 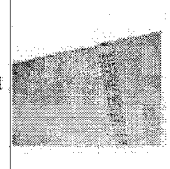 | RUST | 0 point(0%) | EVALUATION POINT |
| | | | PEELING OFF | 0 point(0%) | 0 point |
| | | | CHECKING | 0 point | SYNTHETIC JUDGEMENT |
| | | | CHLOROSIS | 0 point | IV |
| | | | SPECTACLE | 0 point | |
| THE OTHERS | | | | | |

FIG. 8
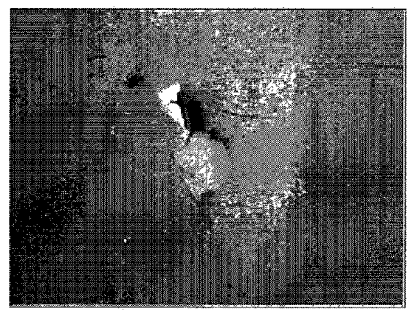
(a) scale image
(b) extraction of gray scale boundary line
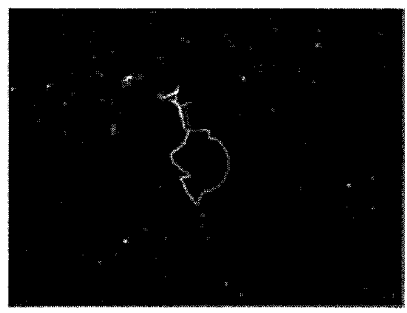
(c) extraction of color tone boundary line FIG. 9
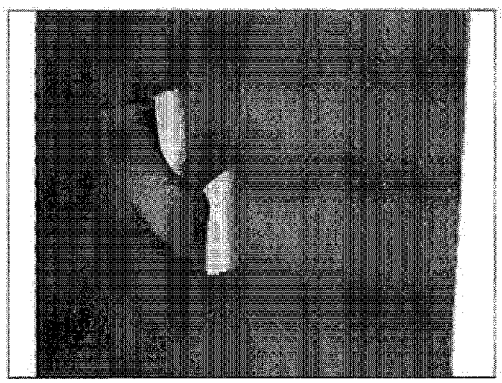
(a) image showing color tone difference
(b) image showing brightness difference FIG. 10
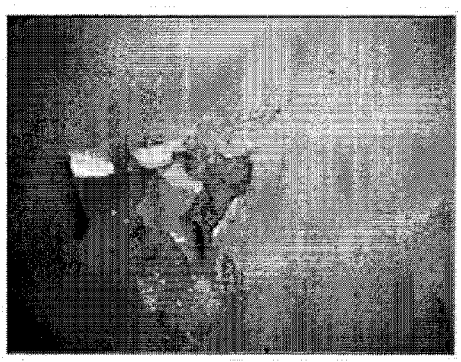
(a) scale image
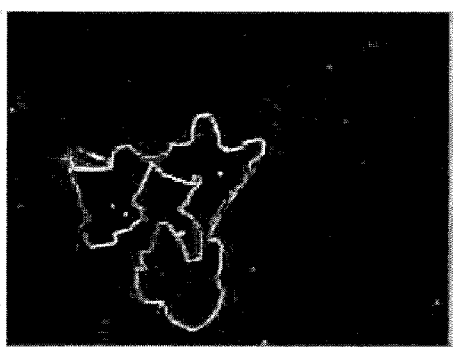
(b) boundary line extraction
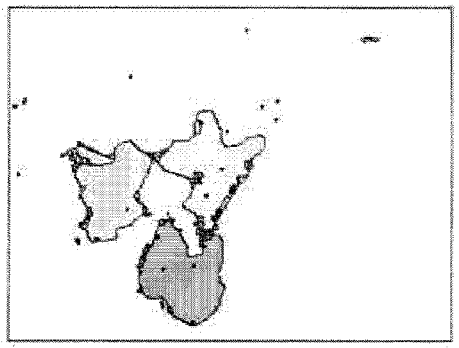
(c) region division
(d) result of scale extraction FIG. 11
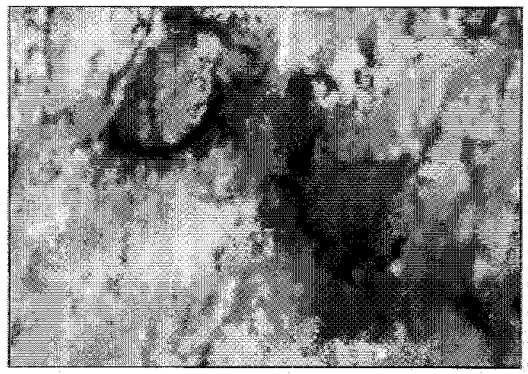
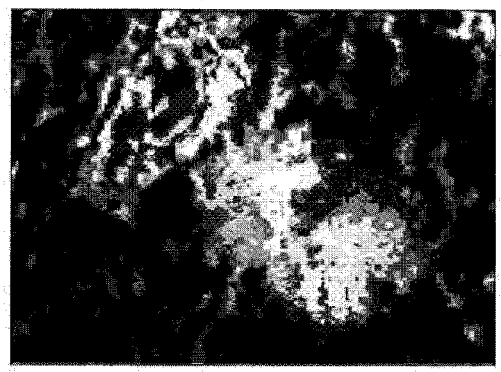
(a) rust image        (b) illustration by rust probability FIG. 12
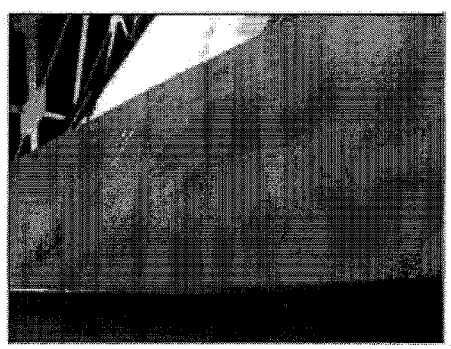
(a)
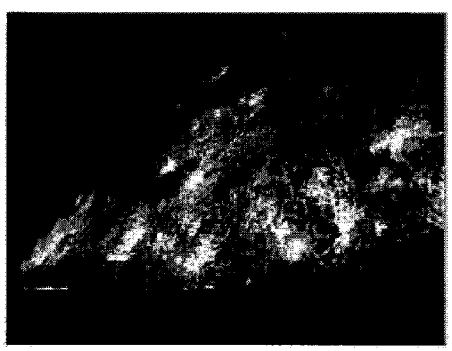
(b)
(c)
(d)

STEEL BRIDGE COATING INSPECTION SYSTEM USING IMAGE PROCESSING AND THE PROCESSING METHOD FOR THE SAME

TECHNICAL FIELD

The present invention relates to an inspection system for paint coated film of steel bridge and a processing method thereof using image processing technique, more particularly, to an inspection system for paint coated film of steel bridge and a processing method thereof using image processing technique that automatically detects rust and scale using color tone information from a photograph file of paint coated film of steel bridge, image processing, water shade and Parzen Window.

BACKGROUND ART

Generally, steel used in various constructions like steel bridge and so on has increased in its number and size, and became important and indispensable material for the modern civilization. While, since these materials have serious fault like deterioration or corrosion by an environment in which they are used, their usage has lot of impediments. Particularly, metallic materials most of which are steel, reduced from stable natural metallic oxides (in rust form) by applying lots of energy to be a useful material for practical use, are unstable and have natural corrosive tendency to turn back to their more stable state.

Therefore, a corrosion loss of the metallic materials amounts to as much as 2-3% of the GNP in the western industrialized country according to the recent survey. A cost from the loss directly from the metal corrosion amounts to 250 billion dollars annually according to the 2002 US statistical data. Of course, if the indirect loss is counted such as suspension by corrosion related repair or stoppage of operation, decline of efficiency, reconstruction, burdensome design and so on, its economical loss would be enormous.

Further, since the corrosion problem related to the economical aspect may also lead to life casualties, it is important to recognize a seriousness of such corrosion problems.

Serious corrosion problems prevalent in most of the pre-existent facilities and constructions due to negligence of such corrosion problems may bring on public criticism and are currently influencing a risk in safety to their peripheral regions. Moreover, despite this situation, the reality is, an importance of a basic technology which became a common sense in the developed country has not been recognized and, frequently, the basic technology is not considered in a design even in the recent major construction works.

Further, the steel bridges in Korea are being constructed in concrete with steel structure and the steel bridge is coated with a periodic rust resisting paint around most of the main members such as iron reinforcing rod, steel frame or bolt connecting part, welding connected part and so on predicted to be corroded from an initial stage of construction. Meanwhile, despite the above way of coating rust resisting paint, environmental conditions of these constructions became more various and severe by the pollution and the progress of industry, and the constructions cannot sustain their reasonable life spans but deteriorated and continuously cause damages from corrosion loss.

Further, a recent increase of corrosion factors of steel structures by construction of structures in oceanic environment and use of chloride material for removal of snow and the like is bringing out an importance of repair and maintenance of the steel structures, and requiring an economic and efficient management of them. As a life span of the paint coated film is considerably shorter than a life span year of the steel bridge, repainting should be achieved in an appropriate time in order to maintain a fair paint coated film state.

A conventional method of inspecting the paint coated film hereinabove referring to FIG. 1 includes: a storage step S101 that stores image information of deteriorated paint coated film of the steel bridge photographed by still picture or video in memory means;

a deteriorated area calculation step S102 that calculates a characteristic amount such as deteriorated area ratio occupied with faults like rust, scale and so on or images and the like from the photographed image information of the deteriorated paint coated film on the steel bridge after the storage step S101 and;

a deteriorated paint coated film of bridge extraction step S103 that extracts a bridge which brought out a premature or an abnormal deterioration of paint coated film by a remaining life span (time for repainting) based on evaluation for deteriorated paint coated film obtained by the calculated characteristic amount after the deterioration area calculation step S102 and a coated paint film deterioration curve (tendency of deterioration of paint coated film) obtained for every bridge as shown in FIG. 2.

Meanwhile, if the above conventional method of inspecting the paint coasted film is described more specifically, photographs stored in the memory means or image information of the deteriorated paint coated film of the steel images photographed in video are called, and a characteristic amount such as deteriorated area ratio occupied with faults like rust, scale and so on, and shape and the like is extracted. That is, if deteriorated region of the paint coated film (damaged part) such as rust, scale and the like is compared to its surrounded region of normal paint coated film, generally, the deteriorated region is relatively darker and its shape is schematically shown in FIG. 2A.

Even if the method of differentiation by an indicated brightness (the method that determines a darker part of a paint coated film as a deteriorated part and, a brighter part of it compared with a certain indicated brightness as a normal paint coated film part) to extract the deteriorating region from the above images is applied, it cannot obtain a result as good as that from a person's eye sight.

If the brightness does not reach the indicated brightness (critical value), the part is regarded as deteriorated part even if it is not a deteriorated part and, in the contrary, it may not be regarded as a deteriorated part if that part is brighter than the critical value even if it is a deteriorated part as shown in FIG. 2B.

Specifically, a maximum value filter process is performed to an input image of FIG. 2A. The maximum value filter process is a process converting a brightness of one point P in the image to the brightest brightness among its peripheral region. Darker points compared to their peripheral region in a range (filter size) are filled with deteriorated parts changed in brightness identical to their peripheral region (FIG. 2C). Meanwhile, a minimum value filter process is performed to an image of FIG. 2C. Contrary to the maximum value filter process, the minimum value filter process is a process converting a brightness of one point P in the image to the darkest brightness among its peripheral region.

The overall brighter image by the maximum value filter process may be restored back to its original brightness according to the above conversion. However, since a part recognized as a deteriorated part once undergone the maximum value filter process cannot be restored back to its original, an image extracted of only the deteriorated part (darker points compared to their peripheral regions) among the input image of FIG. 2A may be obtained (FIG. 2D). Accordingly, if an image is obtained from FIG. 2A distracted of FIG. 2D, it became an image of only deteriorated part without influenced by a brightness variation. Then, in case that there is a brightness variation in the image, a relatively dark region compared to its peripheral region at respective regions in the image is extracted and recognized as a deteriorated part.

DISCLOSURE

Technical Problem

However, since the conventional method of inspecting paint coated film as above extracts a deteriorated region using only gray level image (brightness), it cannot distinguish a kind of deterioration, that is, distinguishing between rust and scale without reflecting a difference in deterioration according to a kind of deterioration, and an efficient inspection of paint coated state is impossible. That is, though a kind of deteriorations includes rust, scale, checking, choking and so on, the most frequently produced are rust and scale. Paint coating on steel bridge is to prevent corrosion of the steel material, while steel material under paint coated film is actually influenced differently by rust and scale.

Accordingly, since evaluation basis for rust and scale in the conventional method of inspecting paint coated film by its area ratio differs from each other as can be confirmed in table 1, a problem of not able to correctly calculate deterioration and evaluate a proper repainting time with the conventional method of inspecting paint coated film using by only a brightness has occurred.

<Steel Bridge Paint Coated Film Deteriorated Level Evaluation Basis>

Therefore, the present invention is to solve the problems of the conventional art and has an object to provide an inspection system for paint coated film of steel bridge and processing method thereof using image processing technique that separately detects rust and scale which are allotted with larger points among the deterioration level evaluation items in determining whether to repaint the paint coated film.

The other object of the present invention is to provide an inspection system for paint coated film of steel bridge and processing method thereof using image processing technique that can quantitatively diagnose a state of paint coated film of steel bridge by automatically detecting rust and scale using color tone information from a photograph file of photographed paint coated film of steel bridge, image processing, water shade and Parzen Window.

Another object of the present invention is to provide an inspection system for paint coated film of steel bridge and processing method thereof using image processing technique that can predict a time for efficient repainting through performing an inspection for paint coated film of steel bridge using an image processing technique separately dealing rust and scale.

Technical Solution

In order to accomplish objects described hereinabove, the present invention provides an inspection system for paint coated film of steel bridge using image processing technique comprising:

a photograph means that outputs photographs image information of a paint coated film of a steel bridge;

TABLE 1

| item to be evaluated | example | | evaluation of each item | | | | | |
|---|---|---|---|---|---|---|---|---|
| rust | | grade | 40 | 30 | 20 | 10 | 0 | |
| | | area % | ≧3 | 1~3 | 0.3~1 | 0.1~0.3 | <0.1 | |
| scale | | grade | 30 | 24 | 18 | 12 | 6 | 0 |
| | | area % | ≧33 | 17~33 | 10~17 | 3~10 | <3 | 0 |
| checking | | grade | 10 | 5 | 0 | | | |
| | | condition | serious | fair | ok | | | |
| choking | | grade | 10 | 5 | 0 | | | |
| | | condition | serious | fair | ok | | | |
| environmental condition | | grade condition | 10 factory/ city | 8 sea/ seacoast | 6 suburbs/ mountain | 4 city/ factory | 2 sea/ seacoast | 0 suburbs/ mountain |
| | | environmental effect | important | important | important | moderate | moderate | moderate |
| overall evaluation | average grade | | 70~100 | | 40~70 | | 20~40 | below 20 |
| | judgment regarding painting for repair | | urgent need of painting for repair | | repair plan in next year | | painting for repair at appropriate time (close investigation is recommended) | paint for repair is not necessary | a computer unit that displays a percentage of deteriorated area on an output unit and calculates a time for repainting and an optimum method for paint coating after diagnosing a deterioration type of a photograph file of photographed paint coated film photographed by the photograph means and detecting a rust part and a scale part by an image processing process; and a data base (DB) unit that stores the image information of a paint coated film of a steel bridge photographed according to a function control signal of the computer unit, and stores calculated information including a deteriorated image of a paint coated film processed by the image processing process and the time for repainting as well as manages various stored information processed by the inspection system for paint coated film.

The other feature of the present invention provides a processing method of an inspection system for paint coated film of steel bridge using image processing technique comprising:

a paint coated film image storing process that stores in a data base unit a paint coated film image information of a steel bridge photographed by the inspection system for paint coated film;

a paint coated film information loading process that loads paint coated film image information through calling a file containing the paint coated film image information to be inspected which is stored in the a DB unit when an inspection program for paint coated film is executed paint coated film image storing process;

a scale and rust extracting process that displays a scale part and a rust part on an output unit after detecting the rust part and the scale part by an image processing process of the inspection system for paint coated film and storing a calculated percentage of deteriorated area in the DB unit when a diagnosis order of inspection program for paint coated film is executed after the paint coated film information loading process; and a repainting information calculating process that calculates a time for repainting and provides an optimum method for paint coating by deteriorated image information of paint coated film which includesing rust and scale information after the scale and rust extracting process.

Further, another feature of the present invention provides a processing method in an inspection system for paint coated film of steel bridge using image processing technique comprising:

a first process that extracts a boundary line in a steel bridge image by color tone information;

a second process that divides a region by an image of the boundary line extracted in the first process with an application of a water shade;

a third process that designates a paint coated film region in a region divided in the second process and then, detects a scale region through measuring a level of similarity of the designated paint coated film region with the rest region;

a fourth process that generates a rust probability density function using a Parzen Window after the third process;

a fifth process that selects a rust region and a rust candidate region using the rust probability density function generated in the fourth process; and a sixth process that extracts rust through repeating a designation the rust candidate region as rust region, if the rust candidate region is adjacent to the rust region after the fifth process.

Advantageous Effects

In accordance with the present invention, the present invention uses a color tone information from a photograph file of photographed paint coated film of steel bridge, an image processing, water shade and a Parzen Window, and automatically detects rust and scale, thereby has an advantageous effects of (a) quantitatively diagnosing a state of paint coated film and (b) predicting a time for efficient repainting through separately dealing rust and scale.

DESCRIPTION OF DRAWINGS

These and other aspects and advantages of the present invention will become apparent and be more readily appreciated from the following description of the embodiments, taken in conjunction with the accompanying drawings, in which:

FIG. 7 illustrates one exemplary result calculated according to the method of the present invention;

FIG. 8 illustrates a method of extracting a color tone boundary line according to the method of the present invention;

FIGS. 9A and 9B illustrate a color tone difference realized according to the method of the present invention;

FIG. 10A through 10D illustrate a process of extracting scale according to the method of the present invention;

FIGS. 11A through 11B illustrate rust image realized according to the method of the present invention; and FIGS. 12A through 12D illustrate a process of extracting rust according to the method of the present invention.

BRIEF DESCRIPTION OF MAIN ELEMENTS

Figure 1:
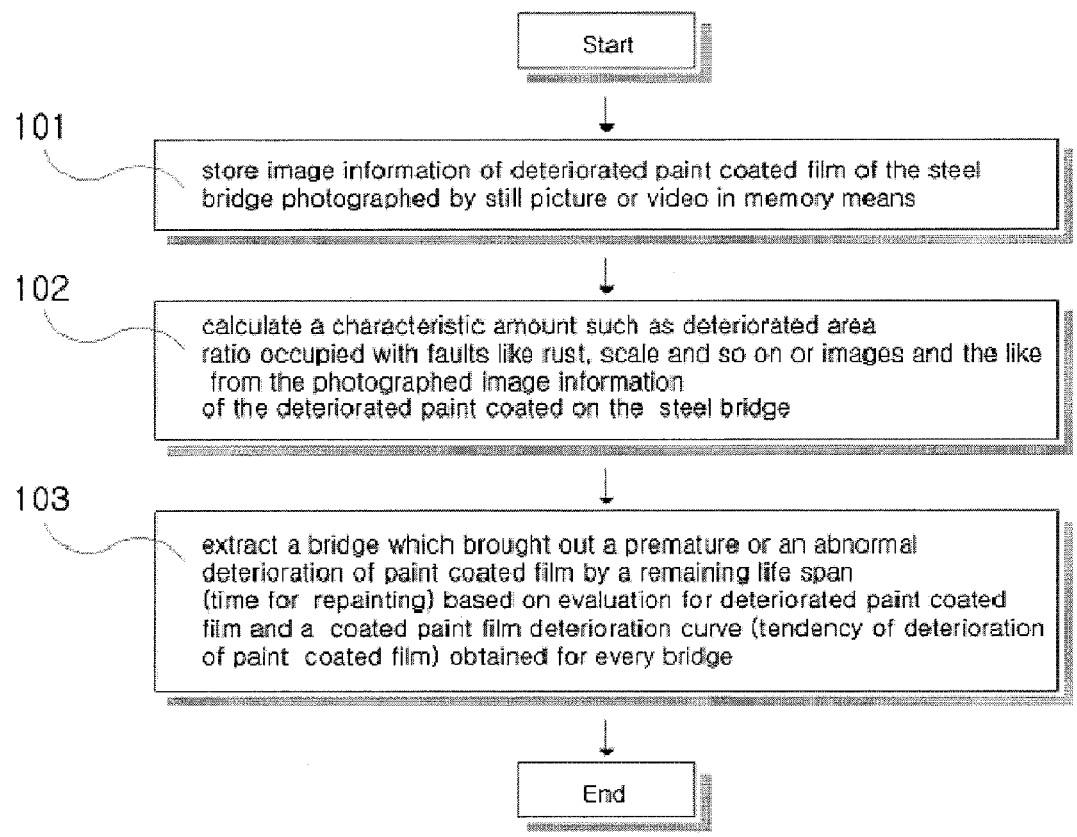
FIG. 1 is a flow chart describing a conventional paint coated film inspection system.
Figure 2:
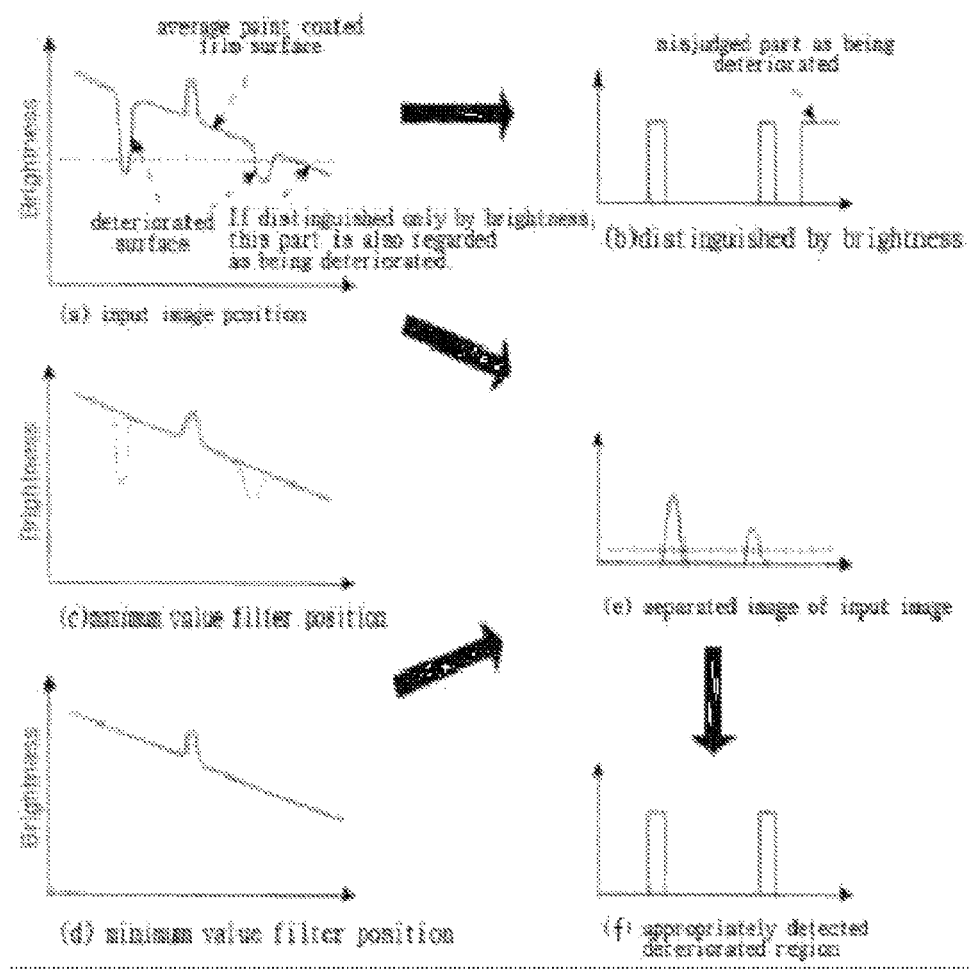
FIGS. 2(a) through 2(f) illustrate one example of paint coated film inspection method by a conventional paint coated film inspection system.

1: photograph means 2: output unit
3: computer unit 4: inspection system for paint coated film
5: data base unit 6: input unit

BEST MODE

Figure 3:
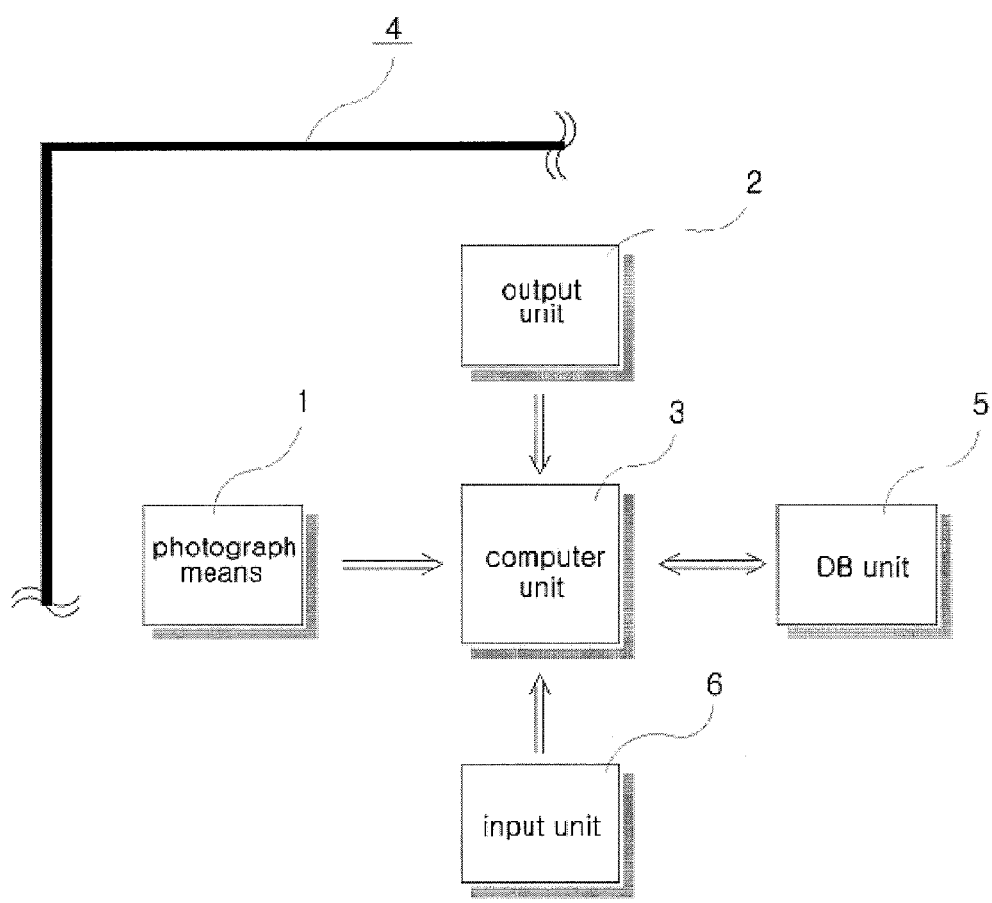
FIG. 3 is a block diagram of paint coated film inspection system according to the present invention.

An inspection system for paint coated film 4 as illustrated in FIG. 3 comprises:

a photograph means 1 that outputs photographs image information of a paint coated film of a steel bridge;

a computer unit 3 that displays a percentage of deteriorated area on an output unit 2 and calculates a time for repainting and an optimum method for paint coating after diagnosing a deterioration type of a photograph file of photographed paint coated film photographed by the photograph means, for example, detecting a rust part and a scale part by an image processing process; and a data base (DB) unit 5 that stores the image information of a paint coated film of a steel bridge photographed according to a function control signal of the computer unit 3, and stores calculated information including a deteriorated image of a paint coated film processed by the image processing process and the time for repainting as well as manages various stored information processed by the inspection system for paint coated film 4.

Here, at one end part of the computer unit 3 is connected to an input unit 6 inputting various control signals. Further, the photograph means includes a digital camera, an analogue camera, a camcorder, a scanner and the like. The output unit 2 includes a monitor or a printer.

Next, a processing method of inspecting paint coated film applied to the paint coated film inspection system for paint coated film 4 of the present invention will be described.

Figure 4:
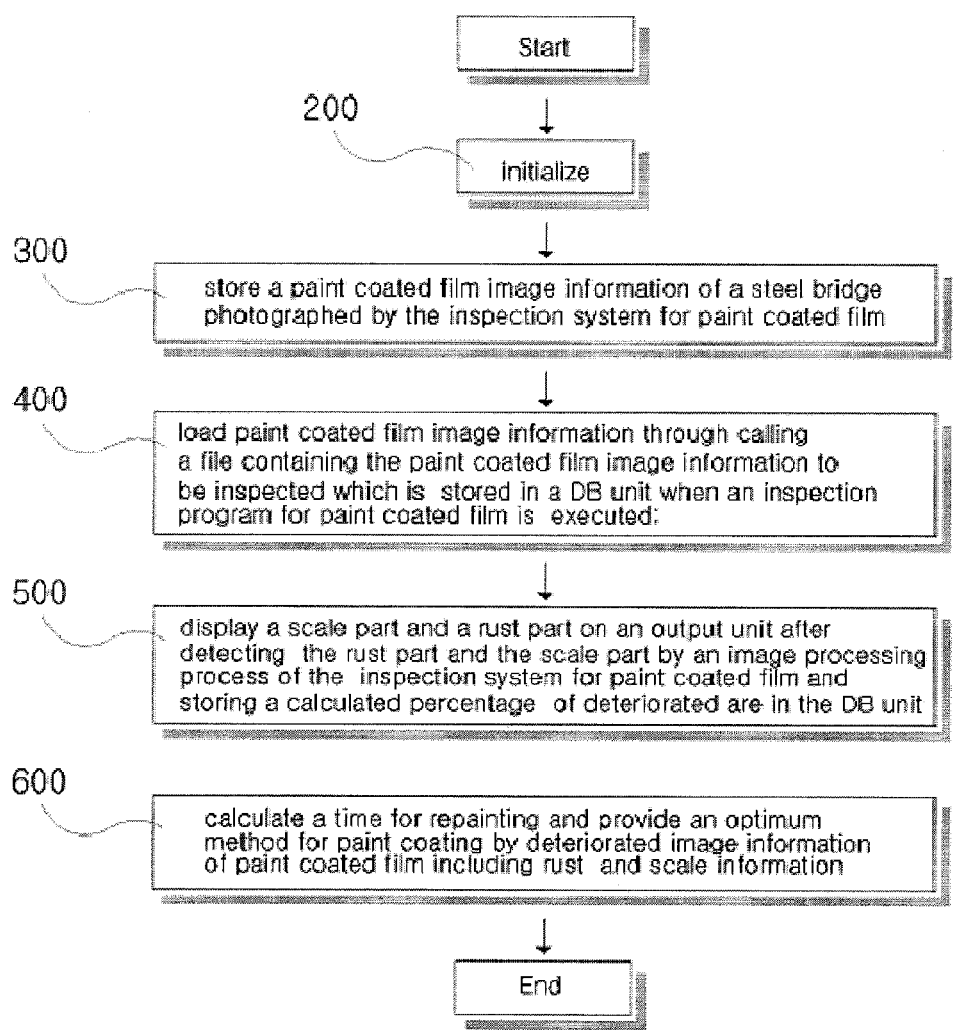
FIG. 4 is a flow chart of paint coated film inspection method according to the present invention.
Figure 5:
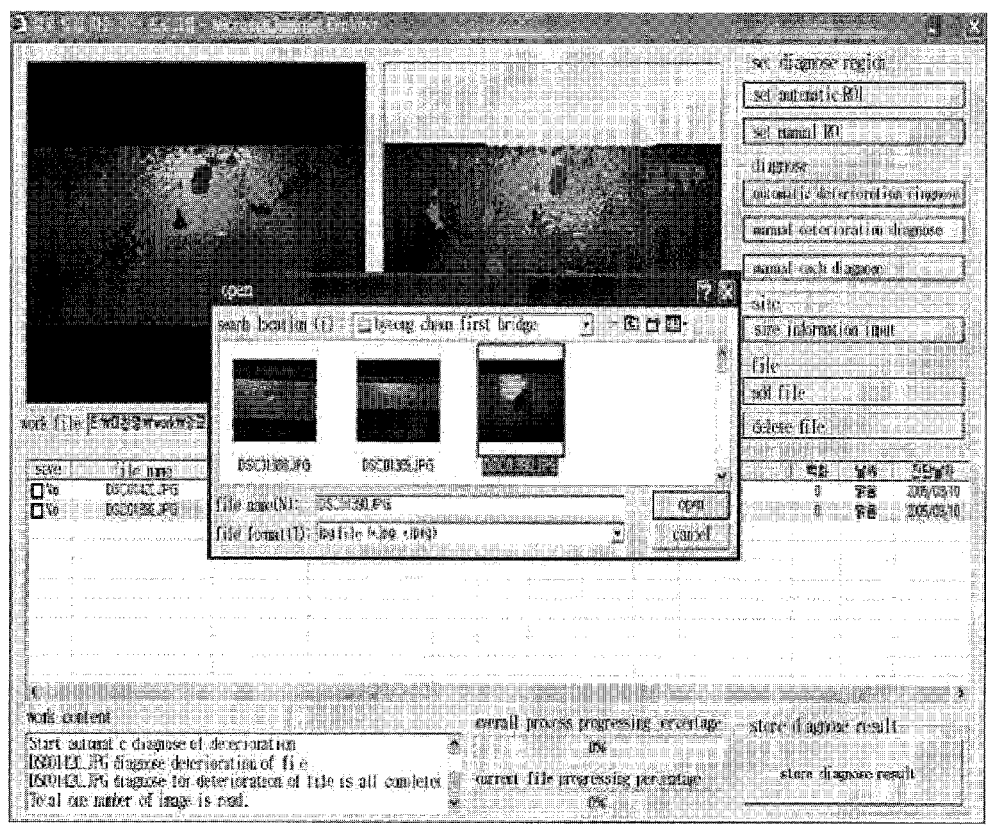
FIG. 5 illustrates an initial screen that starts a diagnosis ofes deterioration by paint coated film inspection method according to the present invention.
Figure 6:
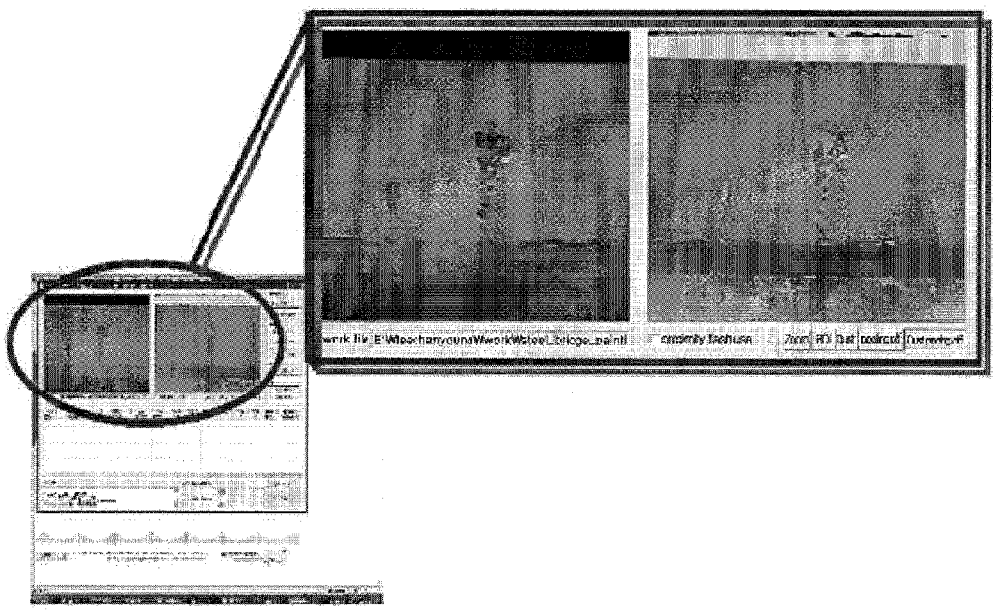
FIG. 6 illustrates a photograph image-processed from an original file photograph illustrating according to one method of the present invention.

The processing method of the present invention as illustrated in FIG. 4 starts from initializing process S200 and progresses to a paint coated film image storing process S300 that stores in the DB unit 5 a paint coated film image information of a steel bridge photographed by the inspection system for paint coated film 4. As shown in FIG. 5, the processing method progresses to a paint coated film information loading process S400 that loads the paint coated film image information is progressed through calling a file containing the paint coated film image information to be inspected which is stored in the DB unit 5 when an inspection program for paint coated film is executed after paint coated film image storing process S300. Then, as shown in FIG. 6, the processing method progresses to a scale and rust extracting process S500 is progressed that displays a rust part and a scale part on the output unit 2 after detecting the rust part and the scale part by the an image processing process of the inspection system for paint coated film 4 and storing a calculated percentage of deteriorated area in the DB unit 5 when a diagnosis order of inspection program for paint coated film is executed after the paint coated film information loading process.

Further, the processing method progresses to a repainting information calculating process S600 is progressed that calculates a time for repainting and provide an optimum method for paint coating by deteriorated image information of paint coated film including rust and scale information after the scale and rust extracting process S500.

Here, the rust and scale extracting process S500 further comprises: a process S501 that extracts a boundary line in a steel bridge image by color tone information;

a process S502 that divides a region by an image of the boundary line extracted in the process S501 with an application of a water shade;

a process S503 that designates a paint coated film region in a region divided in the process S502 and then, detects a scale region through measuring a level of similarity of the designated paint coated film region with the rest region.

Further, the scale and rust extracting process S500 comprises a process S511 that generates a rust probability density function using a Parzen Wwindow;

a process S512 that selects a rust region and a rust candidate region using the rust probability density function generated in the process S511; and a process S513 that extracts rust through repeating a designation the rust candidate region as rust region from, if the rust candidate region is adjacent to the rust region after during the process S512.

As described above, rust and scale necessary for calculating a deterioration level of a steel bridge are possible to be distinguished and detected a scale through a scale extracting process and a rust extraction process of the scale and rust extracting process S500.

Here, during the scale extracting process, scale can be efficiently detected through using a water shade algorithm and measuring a similarity level in a color tone space, and during the rust extracting process, rust can be efficiently and appropriately detected according to a characteristic of rust production through generating a rust probability density function using Parzen Wwindow.

Meanwhile, since inspection completed data through the above scale and rust extracting process S500 is stored in the DB unit 5, and the computer unit 3 of the paint coated film inspection system for paint coated film 4 can call the inspection result at any time on the output unit 2, that is a monitor, as shown in FIG. 7, a management of a paint coated film inspection record becomes convenient and a repair painting at optimum time is possible to be performed, thereby an efficiency of maintenance and management is expected to be enhanced.

In other words, a boundary line is detected using a color tone information in process 501 of the scale extracting process. The color tone information should be used to correctly obtain the boundary line information since the information used to distinguish a region is the boundary line information between the regions.

Here, to extract the boundary line using the above color tone value, is detected by using the boundary line is detected through using a maximum value among elements of boundary line in each channel after obtaining a boundary line through using a sobel mask on respective channels in RGB color tone space.

That is, FIG. 8B is a picture of a boundary line extracted from the image of FIG. 8A in gray level, and FIG. 8C shows the extracted result of the color tone boundary line. Here, the boundary line is more clearly detected in FIG. 8C than in FIG. 8B.

Further, in the process 502 of the scale extracting process, the image is divided into a region of identical color tone by applying the water shade algorithm to an image of the color tone boundary line extracted in the prior process.

Here, the water shade algorithm is researched in the field of geomorphology that regards an image as a three dimensional terrain relating a pixel value to height, and, divides the image through judging a puddle surrounded by one water level contour line made of water level made from pouring watered into the terrain as a divided region.

In addition, the paint coated region is designated, and then, the scale region is detected through measuring the similarity level compared with the rest region in the process 503 of the scale extracting process.

That is, as shown in FIG. 8, the paint coated film and the scale are distinguished from each other for two cases, when there is a big difference in color tone and, a big difference in brightness. FIG. 9A shows a big difference in color tone between the paint coated film and the scale and, FIG. 9B shows a big difference in brightness. Using this, the scale is distinguished by measuring the similarity level with the paint coated film.

In other words, since the largest region inside the steel bridge region to be diagnosed in the scale extracting process is the paint coated film, the largest region among the previously divided regions is allocated as paint coated film. Then, the rest region is distinguished as paint coated film or scale through measuring the similarity level of color tone or brightness compared with the region initially set as paint coated region.

Here, a representative value for the measuring the similarity level uses an averages of color tone and brightness information of the respective regions. A formula for measuring the similarity level follows the next mathematical equation 1.

$$\max(\|P_{ch}-C_{ch}\|,\|P_{lu}-C_{lu}\|) > T_{peeling} \quad \text{[equation 1]}$$

where, P is paint coated region and C is the region to be compared.

Vector elements of one pixel are represented by color tone information 'ch⊙ and brightness information 'lu'. $T_{peeling}$ is a threshold value for measuring the similarity level of color tone or brightness.

Therefore, a region showing a big difference of brightness or color tone in measuring the similarity level is detected as scale. The above mathematical equation 1 distinguishes paint coated film and scale using a value showing a big difference of brightness information and color tone information considering such aspects.

Consequently, referring to FIG. 10 of the scale extracting process, a result of the detected boundary line is shown in FIG. 10B through applying the color tone boundary line extracting algorithm to the image of FIG. 10A.

Moreover, FIG. 10C is the result of applying the water shade algorithm to FIG. 10B, and FIG. 10D is the result extracting the scale region through measuring the similarity level with the paint coated film. The paint coated region is represented in black and the scale region is represented in gray.

Meanwhile, in the rust extracting process, the probability density function to distinguish rust based on probability obtains rust through applying the Parzen Window method to color image data which is manually extracted of rust from steel bridge image having rust.

Most of all, if the Parzen Window is used, the rust extracting process can be modeled by an arbitrary probability distribution without depending on a parameter of polynomial expression.

One characteristic of the rust is that the rust is oxidized and spread from the first oxidized place spot as a starting point.

Therefore, a probability to be a rust region is relatively high for the pixel around the rust region.

In the rust extracting process, the pixel of the image in FIG. 11A is represented by different brightness dependent on the rust production probability in FIG. 11B. The pixel of rust production probability 0 is represented as black color and, as the rust production probability increases, the pixel is represented in color closer to white color as shown in FIG. 11B. As shown in FIG. 11B, a rust sample of very high probability exists at a center of rust part and a sample of lower rust probability exists as it moves farther from the center.

That is, in order to detect the rust, first, a part of higher probability to be rust is distinguished and a part of less probability to be rust is regarded as rust candidate. An initial rust region and a rust candidate region by a color tone of the pixel are determined by the following mathematical equation 2.

$$I(x, y) = \begin{cases} \text{rust} & p(a|\text{rust}) > T_{rust} \\ \text{candidate} & T_{rust} > p(a|\text{rust}) > 0 \\ \text{non-rust} & \text{otherwise} \end{cases} \quad [\text{equation 2}]$$

where I(x,y) represent the pixel at point (x,y). 'a'⊙ is a vector having color tone information at point (x,y) and p(a|rust) is the rust probability density function. $T_{rust}$ is a probability value used for designating the initial rust region.

Therefore, in the rust extracting process, the rust region and the rust candidate region are allocated, and the rust candidate around the rust or in the scale region is allocated as rust, which can be represented in the following mathematical equation.

$$\text{if } [\min(\|X_{candidate} - X_{rust}\|) \leq D] \quad [\text{equation 3}]$$
$$\text{then candidate} \leftarrow \text{rust}$$

where $X_{candidate}$ is the rust candidate positional coordinate in the steel bridge image determined by equation 2, and $X_{rust}$ is the rust positional coordinate in the steel bridge image determined by equations 2 and 3. D is distance used to determine a range of region confirming whether there is rust around the rust candidate region.

Equation 3 is repeated to determine the final rust region until there is finally no more pixel that changes from the rust candidate to rust finally in the rust extracting process.

The rust extracting process is shown in stepwise as following table 2.

TABLE 2

Step 1: Rust and rust candidate are selected based on the probability distribution in the steel bridge image.
$I(x,y) = $ rust $\quad$ p (a | rust) > $T_{rust}$
$\quad\quad\quad$ candidate $\quad T_{rust}$ > p (a | rust) > 0
$\quad\quad\quad$ non-rust $\quad$ otherwise
Step 2: Rust candidate is allocated as rust if the rust candidate is adjacent to rust.
if [min (|| $X_{candidate}$ – $X_{rust}$ ||) ≦ D]
$\quad\quad\quad\quad$ then candidate ← rust
Step 3: Repeat step 2 until there is no change from rust candidate to rust.

If the rust extracting process is examined referring to FIG. 12, rust in FIG. 12 is represented in white and rust candidate is represented in gray.

That is, FIG. 12B is the image applied of the rust extracting algorithm Step 1 on the image of FIG. 12A, which shows that the initial rust region of high probability is at the center of the rust candidate region surrounded by the rust candidate region of low probability.

FIG. 12C in the rust extracting algorithm Step 2 is resulted from expanded rust region that shows an expansion to rust candidate region which peripheral region is rust region.

FIG. 12D represents the final rust detected result.

INDUSTRIAL APPLICABILITY

As described in the above description, the present invention automatically detects rust and scale using color tone information from a file of a photographed paint coated film of steel bridge, image processing, water shade and Parzen Window, thereby quantitatively diagnose a state of steel bridge paint coated film and can be conveniently used in diagnosis field of steel bridge paint coated film.

The invention claimed is:

1. An inspection system for paint coated film of steel bridge using image processing technique comprising:
a photograph means that output photograph image information of a paint coated film of a steel bridge;
a computer unit that displays a percentage of deteriorated area on an output unit and calculates a time for repainting and an optimum method for paint coating after diagnosing a deterioration type of a photograph file of photographed paint coated film photographed by the photograph means and separately detecting a rust part and a scale part by an image processing process; and
a data base (DB) unit that stores the image information of a paint coated film of a steel bridge photographed according to a function control signal of the computer unit, and stores calculated information including a deteriorated image of a paint coated film processed by the image processing process and the time for repainting as well as manages various stored information processed by the inspection system for paint coated film.

2. A processing method of an inspection system for paint coated film of steel bridge using image processing technique comprising:
- a paint coated film image storing process that stores in a data base (DB) unit a paint coated film image information of a steel bridge photographed by the inspection system for paint coated film;
- a paint coated film information loading process that loads paint coated film image information through calling a file containing the paint coated film image information to be inspected which is stored in the DB unit when an inspection program for paint coated film is executed after the paint coated film image storing process;
- a scale and rust extracting process that separately displays a scale part and a rust part on an output unit after separately detecting the rust part and the scale part by an image processing process of the inspection system for paint coated film and storing a calculated percentage of deteriorated area in the DB unit when a diagnosis order of inspection program for paint coated film is executed after the paint coated film information loading process; and
- a repainting information calculating process that calculates a time for repainting and provides an optimum method for paint coating by deteriorated image information of paint coated film which includes rust and scale information after the scale and rust extracting process.

3. The processing method of an inspection system for paint coated film of steel bridge using image processing technique according to claim 2, wherein the scale and rust extracting process further comprises:
- a step of extracting a boundary line in a steel bridge image by color tone information;
- a step of dividing a region by an image of the boundary line extracted in the extracting step with an application of a water shade; and
- a step of designating a paint coated film region in a region divided in the dividing step and detects a scale region through measuring a level of similarity of the designated paint coated film region with the rest region.

4. The processing method of an inspection system for paint coated film of steel bridge using image processing technique according to claim 3, wherein the extracting step further comprises a boundary line detecting step to extract a boundary line using a color tone value that detects a boundary line using a maximum value among elements of boundary line in each channel after obtaining a boundary line through using a sobel mask on respective channels in RGB color tone space.

5. The processing method of an inspection system for paint coated film of steel bridge using image processing technique according to claim 3, wherein the measuring a level of similarity in the designating step uses a first algorithm:

$$\max(\|P_{ch}-C_{ch}\|, \|P_{lu}-C_{lu}\|) > T_{peeling}$$

where, P is paint coated region and C is the region to be compared and vector elements of one pixel are represented by color tone information ch and brightness information lu and $T_{peeling}$ is a threshold value for measuring the similarity level of color tone or brightness.

6. The processing method of an inspection system for paint coated film of steel bridge using image processing technique according to claim 2, wherein the scale and rust extracting process further comprises:
- a step of generating a rust probability density function using a Parzen window;
- a step of selecting a rust region and a rust candidate region using the rust probability density function generated in the generating step; and
- a step of extracting rust through repeating a designation the rust candidate region as rust region, if the rust candidate region is adjacent to the rust region after the selecting step.

7. The processing method of an inspection system for paint coated film of steel bridge using image processing technique according to claim 6, wherein the selecting step uses a second algorithm to allocate the rust candidate as the rust region if the rust candidate region is around the rust or in the scale region after allocating the rust and the rust candidate region, wherein the second algorithm is the following:

if $[\min(\|X_{candidate}-X_{rust}\|) \leq D]$ then candidate←rust where $X_{candidate}$ is the rust candidate positional coordinate in the steel bridge image determined by a third algorithm, and $X_{rust}$ is the rust positional coordinate in the steel bridge image determined by the second and third algorithms and D is distance used to determine a range of region confirming whether there is rust around the rust candidate region, wherein the third algorithm is the following:

rust $p(a\backslash\text{rust}) > T_{rust}$ $I(x,y)$=candidate $T_{rust} > p(a\backslash\text{rust}) > 0$ non-rust otherwise where I(x,y) represent the pixel at point (x,y) and 'a' is a vector having color tone information at point (x,y) and $p(a\backslash\text{rust})$ is the rust probability density function and $T_{rust}$ is a probability value used for designating the initial rust region.

8. A processing method in an inspection system for paint coated film of steel bridge using image processing technique comprising:
- a first process that extracts a boundary line in a steel bridge image by color tone information;
- a second process that divides a region by an image of the boundary line extracted in the first process with an application of a water shade;
- a third process that designates a paint coated film region in a region divided in the second process and detects a scale region through measuring a level of similarity of the designated paint coated film region with the rest region;
- a fourth process that generates a rust probability density function using a Parzen window after the third process;
- a fifth process that selects a rust region and a rust candidate region using the rust probability density function generated in the fourth process; and
- a sixth process that extracts rust through repeating a designation the rust candidate region as rust region, if the rust candidate region is adjacent to the rust region after the fifth process,
wherein the method separately detects the scale region and separately selects the rust region.

* * * * *